United States Patent [19]

Ohashi et al.

[11] Patent Number: 5,290,812

[45] Date of Patent: Mar. 1, 1994

[54] PHENOXYALKYLCARBOXYLIC ACID DERIVATIVES AND PROCESS OF PREPARING THE SAME

[75] Inventors: Mitsuo Ohashi, Omiya; Toshio Tanaka, Nogi; Norihisa Ishikawa, Oyama; Tetsuya Kishi, Konosu, all of Japan

[73] Assignee: Kyorin Pharmaceutical Co., Ltd., Tokyo, Japan

[21] Appl. No.: 814,477

[22] Filed: Dec. 30, 1991

[30] Foreign Application Priority Data

Jan. 18, 1991 [JP] Japan .................. 3-054207
Dec. 26, 1991 [JP] Japan .................. 3-359460

[51] Int. Cl.$^5$ .................. A61K 31/19; A61K 31/235; C07C 323/22; C07C 69/612
[52] U.S. Cl. .................. 514/545; 514/571; 560/9; 560/17; 560/61; 560/62; 562/431; 562/471; 562/472
[58] Field of Search .......... 560/9, 17, 61, 62; 562/431, 471, 472; 514/545, 571

[56] References Cited

FOREIGN PATENT DOCUMENTS 0150447 8/1985 European Pat. Off. .
0306959 3/1989 European Pat. Off. .
0332109 9/1989 European Pat. Off. .

*Primary Examiner*—José G. Dees
*Assistant Examiner*—Vera C. Clarke
*Attorney, Agent, or Firm*—Oblon, Spivak, McClelland, Maier & Neustadt

[57] ABSTRACT

Phenoxyalkylcarboxylic acid derivatives represented by the following formula (I)

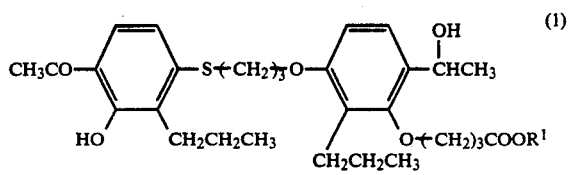

having a strong and selective leukotriene antagonistic action and useful for prophylaxis and therapy of allergic diseases as asthma and processes of preparing the same.

5 Claims, No Drawings

PHENOXYALKYLCARBOXYLIC ACID DERIVATIVES AND PROCESS OF PREPARING THE SAME

BACKGROUND OF THE INVENTION

The present invention concerns novel phenoxyalkylcarboxylic acid derivatives having a strong and selective leukotriene antagonistic action and useful for prophylaxis and therapy of allergic diseases as asthma, and processes of preparing the same.

The leukotrienes (leukotriene $C_4$, $D_4$, $E_4$), which are metabolites of arachidonic acid through 5-lipoxygenase pathway, are the components of SRS-A (slow reaction substance of anaphylaxis) considered to be a major etiogenic substance of immediate type allergic diseases such as bronchial asthma and so on.

Hence, leukotriene antagonists are expected as a useful anti-allergic agent.

The inventors of the present invention had formerly found that a part of compounds of phenoxyalkylcarboxylic acid derivatives is leukotriene antagonists (Japanese Laid-open Publication No. Hei 2-1459 corresponding to EP 0 332 109 and U.S. Pat. No. 4,985,585), but there has been a desired creative preparation of compounds having activity in vivo.

SUMMARY OF THE INVENTION

As the result of diligent study concerning leukotriene antagonists, the inventors of the present invention have found that phenoxyalkylcarboxylic acid derivatives represented by the following general formula (1) have a strong and selective leukotriene antagonistic action, and completed the present invention.

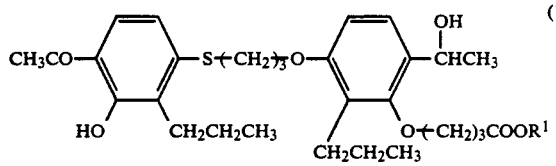

wherein $R^1$ denotes a hydrogen atom, methyl group and ethyl group.

DETAILED EXPLANATION OF THE INVENTION

According to the present invention, the compound of the general formula (1) can be prepared through the routes mentioned below.

(1) A compound of the following general formula (1a) can be prepared by allowing a compound of the general formula (2) to react with a compound of the general formula (3)

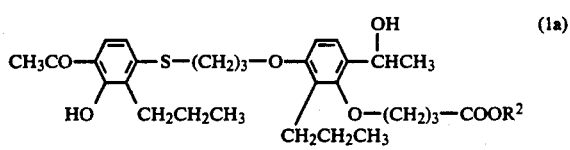

wherein $R^2$ denotes methyl group or ethyl group,

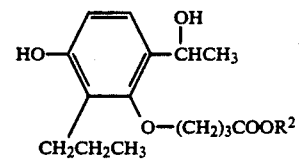

wherein $R^2$ denotes methyl group or ethyl group,

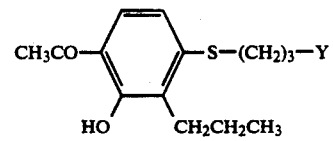

wherein Y denotes a halogen atom.

The reaction is preferably conducted in an organic solvent, for example, acetone, methylethylketone, diethylketone or dimethylformamide etc. at a reaction temperature of room temperature to solvent refluxing temperature. Then, the presence of an inorganic base, for example, potassium carbonate or sodium carbonate etc. and further the addition of potassium iodide are also favorable. A compound of the general formula (1a) can be converted into the corresponding carboxylic acid compound by a conventional method.

(2) A compound represented by the general formula (1) can be prepared by allowing a compound of the general formula (4) to react with a compound of the formula (5), if necessary, followed by hydrolysis thereof:

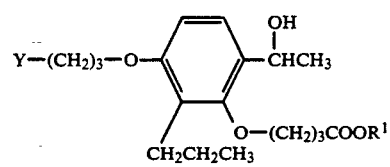

wherein Y denotes a halogen atom and $R^1$ denotes a hydrogen atom, methyl group or ethyl group.

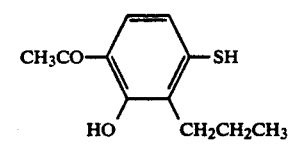

The reaction is conducted according as the method (1) and is preferably conducted in an organic solvent, for example, acetone, methylethylketone, diethylketone or dimethylformamide etc. at a reaction temperature of room temperature to the solvent refluxing temperature. Then, the presence of an inorganic base, for example, potassium carbonate or sodium carbonate etc. and further the addition of potassium iodide are also favorable.

(3) A compound represented by the general formula (7) can be prepared by allowing a compound of the general formula (6) to undergo a catalytic hydrogenation with hydrogen or to react with a reducing agent:

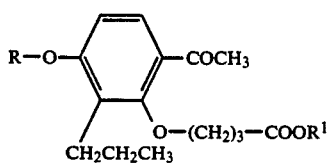

(6)

wherein R denotes a hydrogen atom or halogenopropyl group and $R^1$ denotes a hydrogen atom, methyl group or ethyl group,

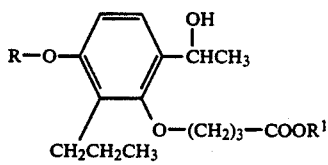

(7)

wherein R and $R^1$ are as mentioned above.

The catalytic hydrogenation with hydrogen is preferably conducted, under the ordinary pressure or an increased pressure, in methanol, ethanol, tetrahydrofuran or dimethylformamide etc. at a reaction temperature of 0° C. to the solvent refluxing temperature. The catalyst to be used is favorably a heterogeneous or homogeneous palladium, nickel, rhodium or ruthenium etc., and furthermore the use of asymmetric catalyst is also favorable.

In case of the reaction with reducing agent, it is preferably allowed to react with the reducing agent, for example, sodium borohydride or lithium aluminum hydride etc. in methanol, ethanol, tetrahydrofuran or dimethylformamide etc. at a reaction temperature of cooling with ice to the solvent refluxing temperature.

In case $R^1$ denotes methyl group or ethyl group in the general formula (7), it can be converted in the corresponding carboxylic acid compound by a conventional method.

Furthermore, the compound represented by the general formula (1) has an asymmetric carbon on 1-position of 1-hydroxyethyl group and so two kinds of optical isomer exist basing on the asymmetric carbon, but the respective isomers or the mixture thereof are all involved in the present invention.

The two kinds of optical isomer can be optically resolved, for example, by forming diastereomeric salt of base such as (S)-(—)-1-(1'-naphthyl) ethylamine with the corresponding carboxylic acid compound or, by taking out with separation using an optically active column. This optical resolution is possible in the compound of the general formula (1) as well as in that of the general formula (7).

Further, the compound represented by the general formula (1), if desired, can be converted into the salt thereof by a conventional method. As the salt thereof, the salt of sodium, potassium, calcium or aluminum etc. is exemplified.

In the following, the present invention is illustrated by the concrete examples, but the present invention never undergoes any restriction by these examples.

EXAMPLE 1

4-[3-[3-(4-acetyl-3-hydroxy-2-propylphenylthio)propoxy]-6-(1-hydroxyethyl)-2-propylphenoxy] butanoic acid (i) A mixture of 8.7 g of ethyl 4-(3-hydroxy-6-(1-hydroxyethyl)-2-propylphenoxy) lactate, 10.21 g of (4-(3-bromopropylthio)-2-hydroxy-3-propylphenyl) ethanone, and 7.79 g of potassium carbonate and acetone (70 ml) was refluxed with heating and stirring. To the reaction mixture were added 2.79 g of (4-(3-bromopropylthio)-2-hydroxy-3-propylphenyl) ethanone after 9 hours and 3.87 g of pottasium carbonate after 9 hours, 11 hours and 16 hours respectively. Then, after the mixture was refluxed with heating and stirring for 18 hours in all, the inorganic matter was filtered off and the filtrate was distilled off under the reduced pressure, The residue was purified through medium pressure silica gel column chromatography (benzene: ethyl acetate=9:1) to afford 13.6 g of crude ethyl 4-[3-[3-(4-acetyl-3-hydroxy-2-propylphenylthio)propoxy]-6-(1-hydroxyethyl)-2-propylphenoxy] butanoate as an oily product (86.5%).

(ii) To a solution of 6.60 g of ethyl 4-[3-[3-(4-acetyl-3-hydroxy-2-propylphenylthio)propoxy]-6-(1-hydroxyethyl)-2-propylphenoxy] butanoate in 10 ml of ethanol was added a solution of 1.41 g of sodium hydroxide in 10 ml of water. After stirred at room temperature for 5 minutes, the mixture was cooled by addition of ice water and washed with ether. To the aqueous layer was acidified with hydrochloric acid and was extracted with ethyl acetate. The organic layer was washed with water, dried over sodium sulfate and concentrated. After the residue was purified through medium pressure silica gel column chromatography (normal phase with methylene chloride: ethanol=100:3, then reverse phase with methanol: water=19:1), it was recrystallized from methanol-water to afford 1.98 g of the aimed product as colorless crystal (31.6%).

Melting point 85°–86° C.

Elementary analysis (%) for $C_{29}H_{40}O_7S$.

| Calculated value (Observed value) | |
|---|---|
| C: 65.39 (65.20) | H: 7.57 (7.63) |

EXAMPLE 2

Ethyl 4-(3-hydroxy-6-(1-hydroxyethyl)-2-propylphenoxy) butanoate 16.4 g of ethyl 4-(6-acetyl-3-hydroxy-2-propylphenoxy) lactate was dissolved into 90 ml of ethanol and added with 1.2 g of 5% palladium-on-charcoal, the mixture of which was then subjected to catalytic hydrogenation with hydrogen under the atmospheric pressure with water cooling.

After completion of the reaction, the catalyst was filtered off and the filtrate was concentrated. The residue was purified through medium pressure silica gel column chromatography (benzene: ethyl acetate=7:3) to afford 14.0 g of the aimed product being light yellow oily (84.8%).

| $^1$H-NMR (CDCl$_3$) δ: | |
|---|---|
| 0.98 | (3H, t, J=7Hz), |

-continued

| ¹H-NMR (CDCl₃) δ: | |
| --- | --- |
| 1.28 | (3H, t, J=7Hz), |
| 1.48 | (3H, d, J=6Hz), |
| 1.58 | (2H, m), |
| 2.14 | (2H, m), |
| 2.4–2.6 | (5H, m), |
| 3.8–3.9 | (2H, m), |
| 4.17 | (2H, q), |
| ~5.1 | (1H, m), |
| 5.65 | (1H, s), |
| 6.56 | (1H, d, J=9Hz), |
| 7.11 | (1H, d, J=9Hz). |

EXAMPLE 3

Ethyl 4-[3-(3-chloropropoxy)-6-(1-hydroxyethyl)-2-propylphenoxy] butanoate

To a solution of 15.0 g of ethyl 4-[6-acetyl-3-(3-chloropropoxy)-2-propylphenoxy] butanoate in 195 ml of methanol was added 2.9 g of sodium borohydride in portions of small quantity under ice cooling and the mixture was stirred at the same temperature for two hours. To the reaction mixture was added 100 ml of water and the solvent was distilled off under reduced pressure. Then, the mixture was acidified with 2N-hydrochloric acid under ice cooling, followed by extraction with ethyl acetate. The organic layer was distilled off under reduced pressure to afford 14.6 g of the aimed product as light yellow oily matter (96.8%).

| NMR (CDCl₃) δ: | |
| --- | --- |
| 0.96 | (3H, t, J=7Hz), |
| 1.27 | (3H, t, J=7Hz), |
| 1.40–1.80 | (2H, m), |
| 1.47 | (3H, d, J=6.6Hz), |
| 2.00–2.40 | (4H, m), |
| 2.40–2.70 | (5H, m), |
| 3.70–4.00 | (4H, m), |
| 4.00–4.30 | (4H, m), |
| 5.10 | (1H, q, J=6.6Hz), |
| 6.70 | (1H, d, J=8.4Hz), |
| 7.20 | (1H, d, J=8.8Hz). |

EXAMPLE 4

4-[3-(3-chloropropoxy)-6-(1-hydroxyethyl)-3-propylphenoxy] butanoic acid

To a solution of 14.6 g of ethyl 4-[3-(3-chloropropoxy)-6-(1-hydroxyethyl)-2-propylphenoxy] butanoate in 85 ml of ethanol was dropwise added 33.3 ml of an aqueous solution of 1.67 g of sodium hydroxide under ice cooling. After stirred for an hour as it was and then allowed to react for 4 hours at room temperature, 5 ml of aqueous solution of 250 mg of sodium hydroxide was twice supplemented to the reaction mixture with interval of an hour to allow the reaction proceeds. After addition of 1N hydrochloric acid under ice cooling to acidify and distillation off of the solvent under reduced pressure, the reaction mixture was alkalilized with 5% aqueous solution of sodium hydroxide and washed with ethyl acetate. The aqueous layer was acidified with 1N hydrochloric acid and extracted with ethyl acetate. The organic layer was dried over anhydrous sodium sulfate after washed with water and saturated aqueous solution of sodium chloride. It was subjected to distillation off of the solvent under reduced pressure to afford 12.9 g of the aimed product as light yellow oily matter (yield 95.1%).

| NMR (CDCl₃) δ: | |
| --- | --- |
| 0.95 | (3H, t, J=7.3Hz), |
| 1.38–1.80 | (2H, m), |
| 1.47 | (3H, d, J=6.6Hz), |
| 2.00–2.40 | (4H, m), |
| 2.40–2.75 | (4H, m), |
| 3.62–3.94 | (4H, m), |
| 4.08 | (2H, t, J=5.7Hz), |
| 5.12 | (1H, q, J=6.6Hz), |
| 6.66 | (1H, d, J=8.8Hz), |
| 7.22 | (1H, d, J=8.8Hz). |

EXAMPLE 5

(+)-4-[3-(3-chloropropoxy)-6-(1-hydroxyethyl)-2-propylphenoxy] butanoic acid and (−)-4-[3-(3-chloropropoxy)-6-(1-hydroxyethyl)-2-propylphenoxy] butanoic acid To a solution of 5.0 g of 4-[3-(3-chloropropoxy)-6-(1-hydroxyethyl)-2-propylphenoxy] butanoic acid in 7 ml of ethyl acetate was added 2.15 ml of (s)-(−)-1-(1-naphthyl) ethylamine, which was then allowed to stand for overnight. The precipitate was collected by filtration and dried after washing with cold ethyl acetate to afford 1.07 g of crude salt. The crude salt was three times recrystallized from ethyl acetate to afford 68.0 mg of (s)-(−)-1-(1-naphthyl) ethylamine salt of (+)-4-[3-(3-chloropropoxy)-6-(1-hydroxyethyl)-2-propylphenoxy] butanoic acid (melting point 124.0°–125.0° C., $[\alpha]_D^{20} + 4.1°$ (c=1.05, ethanol)). This salt was acidified with 1N hydrochloric acid under ice cooling and extracted with ethyl acetate. After washed with water and saturated aqueous solution of sodium chloride, the organic layer was dried over anhydrous sodium sulfate and subjected to distillation off of the solvent under reduced pressure to afford 42.6 mg of (+)-4-[3-[3-chloropropoxy)-6-(1-hydroxyethyl)-2-propylphenoxy] butanoic acid as slightly yellow oily matter. $[\alpha]_D^{20} + 19.0°$ (c=0.852, ethanol) The filtrate separated from the crude salt was acidified with 1N hydrochloric acid under ice cooling and extracted with ethyl acetate. After washed with water and saturated aqueous solution of sodium chloride, the organic layer was dried and subjected to distillation off of the solvent to afford 4.45 g of residue, which was then dissolved into 7 ml of ethyl acetate, added with 1.92 ml of (R)-(+)-1-(1-naphthyl) ethylamine and allowed to stand for overnight. The precipitate was collected by filtration and dried after washing with cold ethyl acetate to afford 1.53 g of crude salt.

The crude salt was three times recrystallized with ethyl acetate to afford 141.4 mg as colorless needle crystal of (R)-(+)-1-(1-naphthyl) ethylamine salt of (−)-4-[3-(3-chloropropoxy)-6-(1-hydroxyethyl)-2-propylphenoxy] lactic acid (melting point 123.0°–124.5° C. $[\alpha]_D^{20} - 4.1°$ (c=1.084, ethanol). To this salt was acidified with 1N hydrochloric acid under ice cooling, which was then extracted with ethyl acetate. After washed with water and saturated aqueous solution of sodium chloride, the organic layer was dried over anhydrous sodium sulfate and subjected to distillation off of the solvent to afford 55.9 mg of (−)-4-[3-(3-chloropropoxy)-6-(1-hydroxyethyl)-2-propylphenoxy] butanoic acid as slightly yellow oily matter. $[\alpha]_D^{20} - 19.1°$ (c=1.034, ethanol)

EXAMPLE 6

(−)-4-[3-(3-(4-acetyl-3-hydroxy-2-propylphenylthio)propoxy)-6-(1-hydroxyethyl)-2-propylphenoxy] butanoic acid A mixed solution of 55.9 mg of (−)-4-[3-(3-chloropropoxy)-6-(1-hydroxyethyl)-2-propylphenoxy] butanoic acid, 39.3 mg of (2-hydroxy-4-mercapto-3-propylphenyl) ethanone, 51.7 mg of potassium carbonate and 1 ml of dimethylformamide was stirred at room temperature for 6 hours. The reaction mixture was poured into ice water, acidified with 1N-hydrochloric acid, and extracted with ethyl acetate. After washed with water and saturated aqueous solution of sodium chloride, the organic layer was dried over anhydrous sodium sulfate and subjected to distillation off of the solvent under reduced pressure to afford residue, which was then purified through silica gel column chromatography (methylene chloride: methanol=20:1) and further purified through preparative thin layer chromatography (methylene chloride: methanol=15:1) to afford 29.8 mg of yellow oily matter as the title compound (35.9%). $[\alpha]_D^{20} - 13.8°$ (c=2.98, ethanol)

| NMR (CDCl$_3$) δ: | |
| --- | --- |
| 0.84–1.17 | (6H, m), |
| 1.37–1.75 | (4H, m), |
| 1.49 | (3H, d, J=6.6Hz), |
| 2.09–2.36 | (4H, m), |
| 2.40–2.78 | (6H, m), |
| 2.58 | (3H, s), |
| 3.19 | (2H, t, J=7.5Hz), |
| 3.74–4.13 | (6H, m), |
| 5.12 | (1H, q, J=6.2Hz), |
| 6.64 | (1H, d, J=8.8Hz), |
| 6.76 | (1H, d, J=8.4Hz), |
| 7.23 | (1H, d, J=8.4Hz), |
| 7.50 | (1H, d, J=8.4Hz), |
| 12.73 | (1H, s). |

EXAMPLE 7

(+)-4-[3-(3-(4-acetyl-3-hydroxy-2-propylphenylthio)propoxy)-6-(1-hydroxyethyl)-2-propylphenoxy] butanoic acid A mixed solution of 42.6 mg of (+)-4-[3-(3-chloropropoxy)-6-(1-hydroxyethyl)-2-propylphenoxy] butanoic acid, 30.0 mg of (2-hydroxy-4-mercapto-3-propylphenyl) ethanone, 39.4 mg of potassium carbonate and 1 ml of dimethylformamide was stirred at room temperature for 4 hours. The reaction mixture was poured into ice water, acidified with 1N hydrochloric acid and extracted with ethyl acetate. After washed with water and saturated aqueous solution of sodium chloride, the organic layer was dried over anhydrous sodium sulfate and subjected to distillation off of the solvent under reduced pressure to afford residue. The residue was purified through silica gel column chromatography (methylene chloride: ethanol=20:1) and further through preparative thin layer chromatography (methylene chloride: methanol=1.5:1) to afford 16.1 mg of yellow oily water as the title compound (yield 25.4%). $[\alpha]_D^{20} + 13.3°$ (c=1.56, ethanol)

| NMR (CDCl$_3$) δ: | |
| --- | --- |
| 0.84–1.17 | (6H, m), |
| 1.37–1.75 | (4H, m), |
| 1.48 | (3H, d, J=6.6Hz), |
| 2.09–2.36 | (4H, m), |
| 2.40–2.78 | (6H, m), |
| 2.58 | (3H, S), |
| 3.19 | (2H, t, J=7.5Hz), |
| 3.56 | (2H, brs), |
| 3.81–4.07 | (4H, m), |
| 5.12 | (1H, q, J=6.6Hz), |
| 6.64 | (1H, d, J=8.8Hz), |
| 6.76 | (1H, d, J=8.8Hz), |
| 7.23 | (1H, d, J=8.4Hz), |
| 7.50 | (1H, d, J=8.4Hz), |
| 12.74 | (1H, S). |

EXPERIMENTAL EXAMPLE 1

Effects on leukotriene D$_4$-induced bronchoconstriction in guinea pigs

Male Hartly guinea pigs weighing about 450 g were anesthetized with sodium pentobarbital (30 mg/kg,i.p.) and the change in intra-tracheal pressure was measured according to modified Konzett-Rössler method (J. Harvey, et al., J. Phamacol. Method, 9, 147–155, 1983). Bronchoconstriction was indused by i.v. injection of leukotriene D$_4$ (3 μg/kg) into the left external jugular vein. Animals were pretreated with i.v. injection of indomethacin and propranolol. The compound of Example 1 as sodium salt solution was i.v. administered 3 min before leukotriene D$_4$ injection. The result was showed in Table 1.

The compound of the present invention showed strong antagonistic action to leukotriene D$_4$ in the isolated guinea pig trachea. Furthermore, the compound intravenously injected inhibited leukotriene D$_4$-induced bronchoconstriction even at a lower dose level.

These results indicate that the compound in the present invention represented by the general formula (1) in useful for treatment of the diseases caused by leukotrienes, such as bronchial asthma, allergy of eye, nose and gastrointestinal tract, allergic dermatitis, circulatory and so on.

TABLE 1

| Tested Compound | Dose (mg/kg, i. v.) | Inhibition (%) |
| --- | --- | --- |
| Example 1 | 0.125 | −0.5 |
| | 0.25 | 45.6 |
| | 0.5 | 56.8 |
| | 1.0 | 71.1 |

What is claimed is:

1. A phenoxyalkylcarboxylic acid derivative or alkali salt thereof represented by a formula (1)

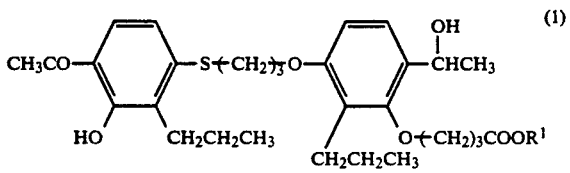

wherein R$^1$ denotes a hydrogen atom, methyl group or ethyl group.

2. A method of preparing a compound of the formula (1) of claim 1, wherein R$^1$ denotes a hydrogen atom characterized in that a compound represented by a formula (2)

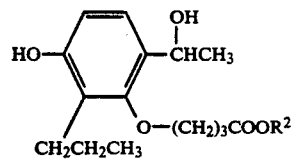

wherein $R^2$ denotes a methyl group or ethyl group is allowed to react with a compound represented by a formula (3)

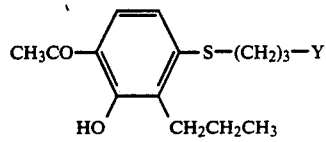

wherein Y denotes a halogen atom to afford a compound of a formula (1a)

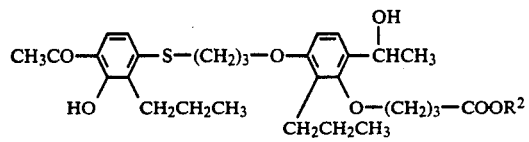

wherein $R^2$ denotes a methyl group or ethyl group, followed by hydrolysis thereof.

3. A method of preparing a compound of the formula (1)

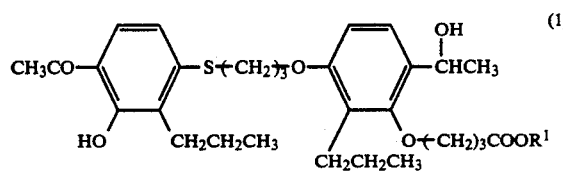

characterized in that a compound represented by a formula (4)

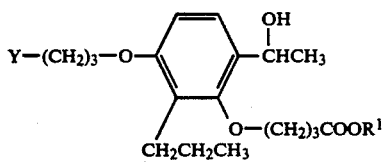

wherein Y denotes a halogen atom and $R^1$ denotes a hydrogen atom, methyl group or ethyl group is allowed to react with a compound represented by formula (5)

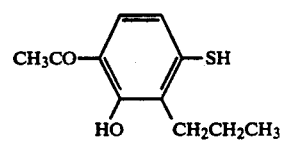

and, if desired, subjected to hydrolysis.

4. A method of preparing a compound represented by a formula (7)

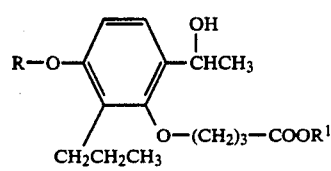

wherein R denotes a hydrogen atom or halogenopropyl group and $R^1$ denotes a hydrogen atom, methyl group or ethyl group characterized in that a compound represented by a formula (6)

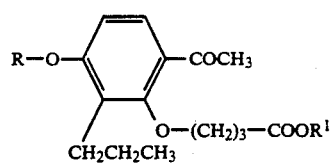

wherein R denotes a hydrogen atom or halogenopropyl group and $R^1$ denotes a hydrogen atom, methyl group or ethyl group is subjected to hydrogenation.

5. An anti-allergenic composition comprising a pharmaceutically effective amount of a phenoxyalkylcarboxylic acid derivative of the formula;

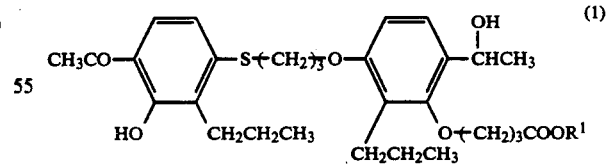

wherein $R^1$ is hydrogen, methyl or ethyl, or an alkali salt thereof in combination with a non-allergenic pharmaceutical carrier.

* * * * *